United States Patent [19]
Saito et al.

[11] Patent Number: 4,982,724
[45] Date of Patent: Jan. 8, 1991

[54] ENDOSCOPE APPARATUS

[75] Inventors: Yoshitake Saito, Kunitachi; Kenji Hirooka, Hachioji, both of, Japan

[73] Assignee: Olympus Opicals Co., Japan

[21] Appl. No.: 286,149

[22] Filed: Dec. 19, 1988

[30] Foreign Application Priority Data

Dec. 28, 1987 [JP] Japan .................................. 62-330291
Jan. 26, 1988 [JP] Japan .................................. 63-7573

[51] Int. Cl.⁵ ............................ A61B 8/12; A61B 1/00
[52] U.S. Cl. ..................................... 128/4; 128/662.6; 73/623
[58] Field of Search .................. 128/4, 662.06; 73/623

[56] References Cited

U.S. PATENT DOCUMENTS

| | | | |
|---|---|---|---|
| 4,433,692 | 2/1984 | Boba | 128/662.06 |
| 4,462,408 | 7/1984 | Silverstein et al. | 128/662.06 |
| 4,548,197 | 10/1985 | Kinoshita | 128/4 A |
| 4,705,023 | 11/1987 | Arai | 128/4 |
| 4,748,969 | 6/1988 | Wardle | 128/4 |
| 4,757,819 | 7/1988 | Yohoi et al. | 128/4 |

FOREIGN PATENT DOCUMENTS 3716963 11/1987 Fed. Rep. of Germany ................... 128/662.06

Primary Examiner—Francis Jaworski

[57] ABSTRACT

In an endoscope apparatus, an ultrasonic vibrating element is rotatably arranged at a distal end of a flexible inserting portion, this ultrasonic vibrating element is rotated by a motor provided in a subsidiary operating portion via a flexible cable extended through the inserting portion, the distal end portion of the inserting portion is bent by operating a handle provided on a primary operating portion, which is arranged at the proximal side of the subsidiary operating portion; a forceps channel is extended through the inserting portion and an opening of the forceps channel is formed in the subsidiary portion. According to such structure, the forceps can be inserted in the forceps channel easily and existing forceps having a standard length can be used as they are.

6 Claims, 7 Drawing Sheets

FIG_1A
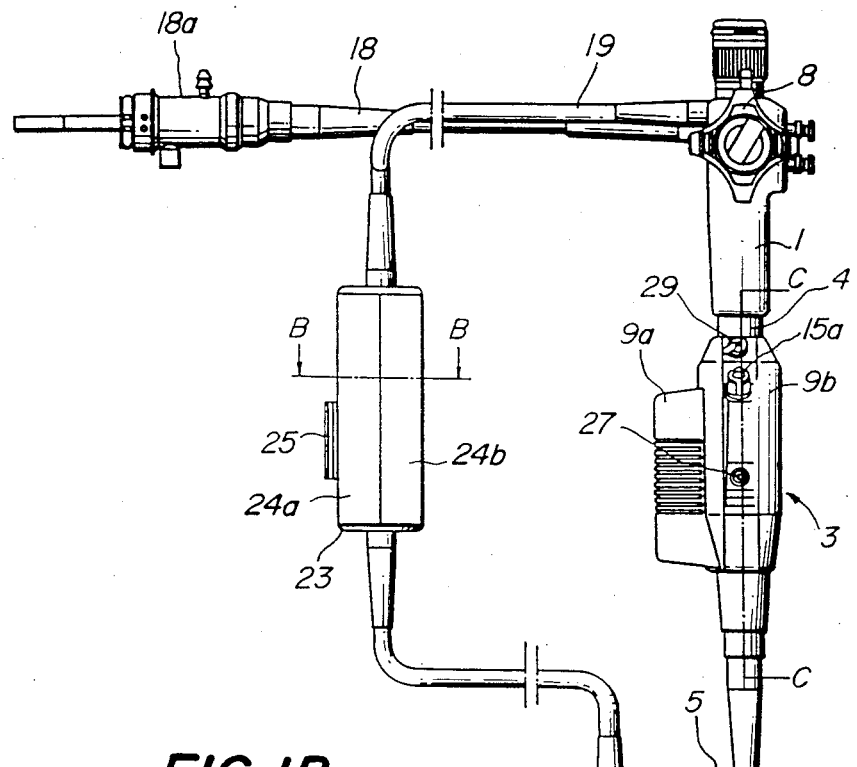
FIG_1B
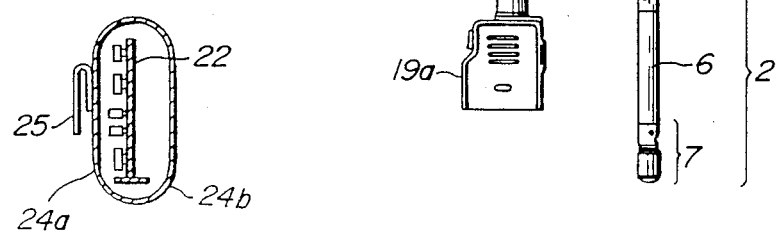

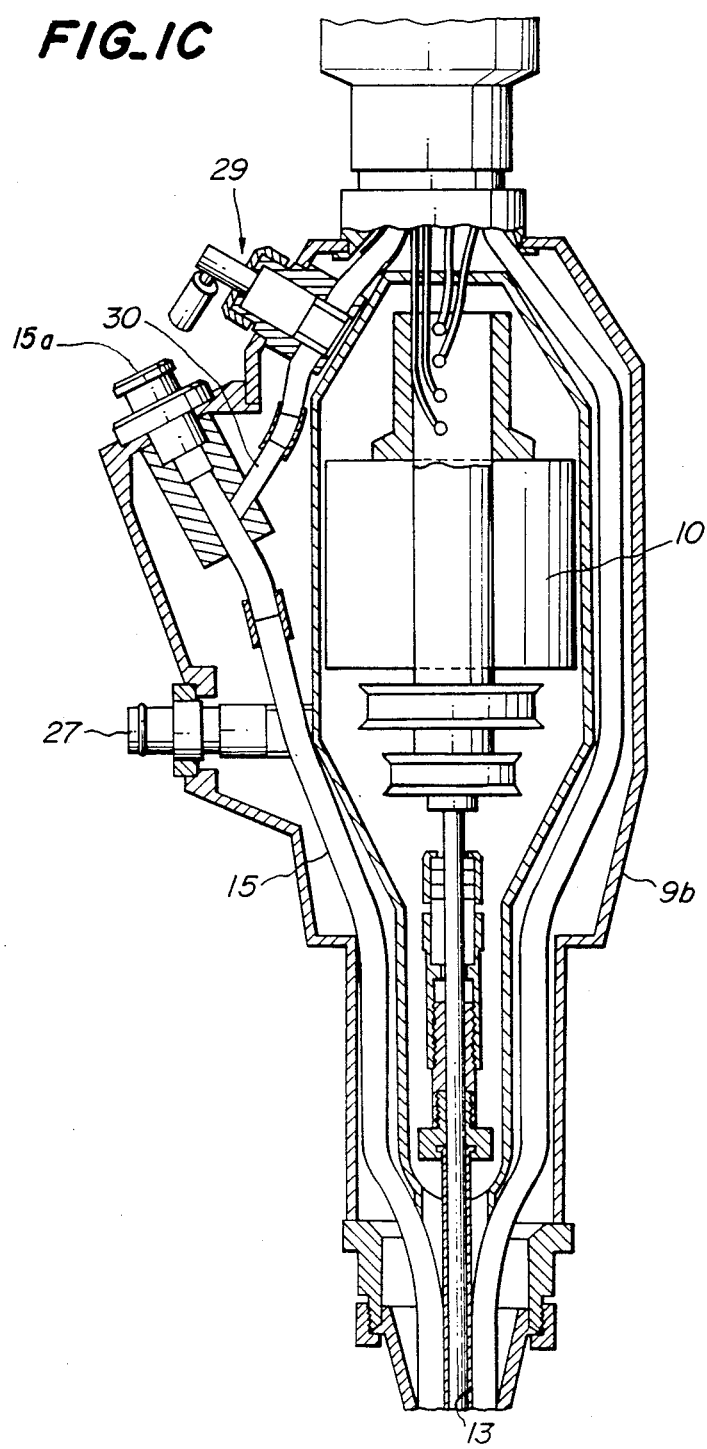
FIG_IC

FIG_2
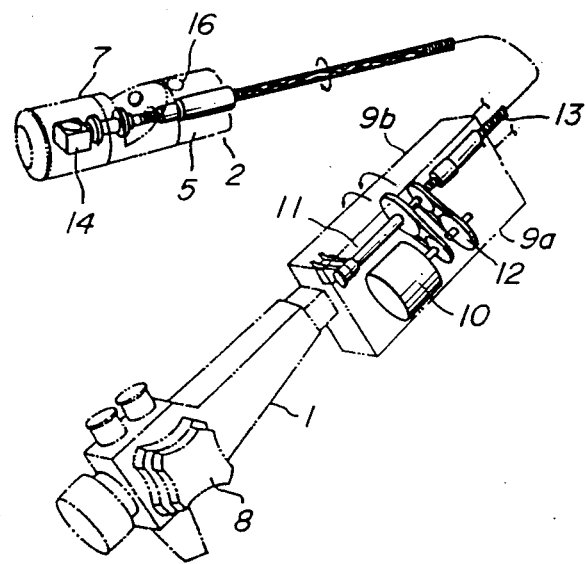
FIG_3
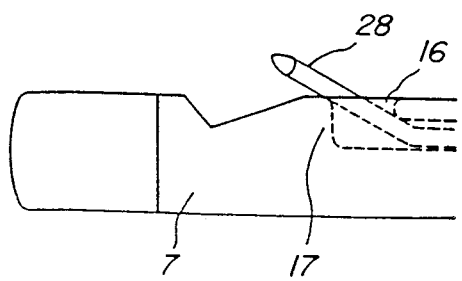

FIG_6
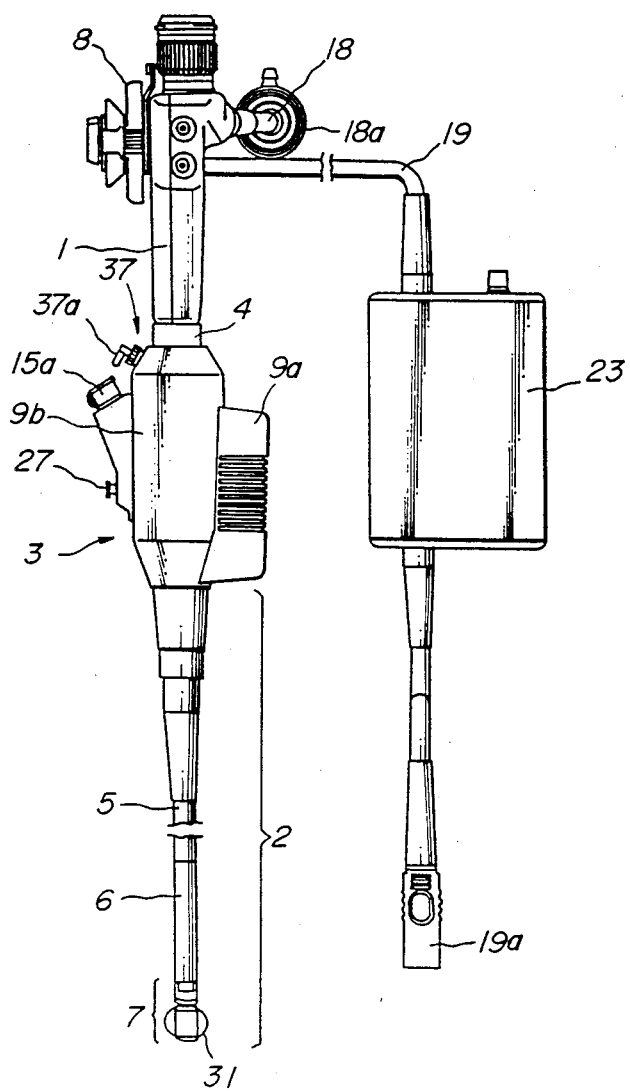

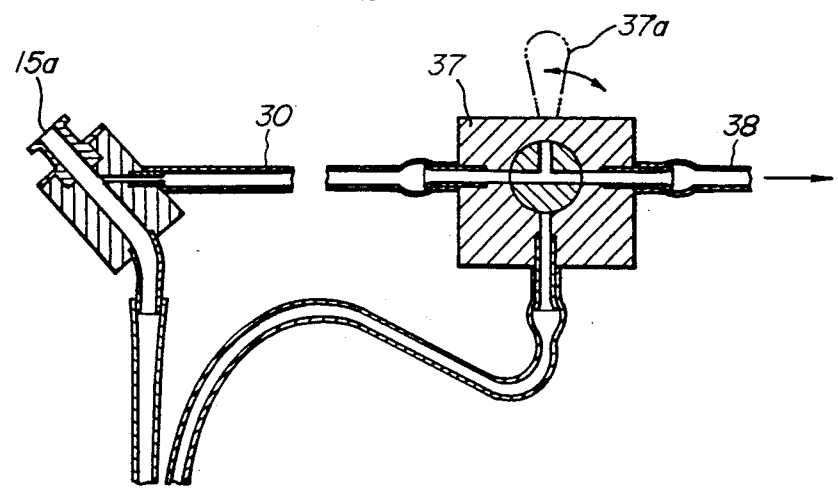
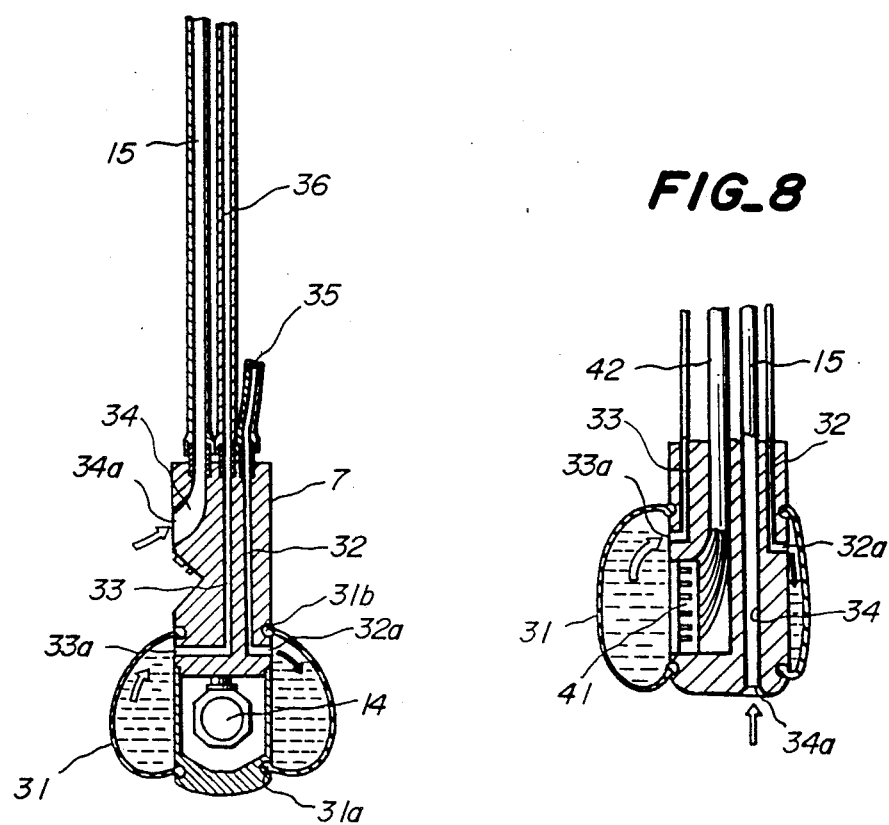
FIG_7
FIG_8

ENDOSCOPE APPARATUS

BACKGROUND OF THE INVENTION

1. Field of the Invention and Related Art Statement

The present invention relates to an endoscope apparatus for use in biopsy for diagnosing insides of cavities. In general, the endoscope apparatus comprises an inserting portion to be inserted in a cavity under the inspection and having distal and proximal ends, a subsidiary operating portion having one end connected to the proximal end of the inserting portion, and a primary operating portion having one end connected to the other end of the subsidiary operating portion.

Various kinds of endoscopes for use in diagnosis or biopsy have been suggested. For example, Japanese Patent Laid-open Publication Kokai Sho No. 60-227,740 discloses an endoscope apparatus in which an ultrasonic vibrating element for transmitting and receiving ultrasonic waves is provided at the distal end portion of a flexible inserting portion, a flexible driving shaft is extended through the inserting portion from the ultrasonic vibrating element up to a subsidiary operating portion, which is connected to the lower portion of a primary operating portion, a driving means is provided in the subsidiary operating portion and the driving power generated thereby is transmitted to the ultrasonic vibrating element via the driving shaft to effect the mechanical scanning for the cavity, a forceps channel is also extended through the inserting portion, and all kinds of forceps are inserted therethrough from an opening formed in the primary operating portion to conduct treatments of biopsy such as collection of living tissues.

However, in such conventional endoscope apparatus, the forceps channel is arranged to be extended from the distal end of the inserting portion to the primary operating portion, so that the forceps opening should be formed in the primary operating portion, and all kinds of forceps have to pass through the subsidiary operating portion arranged between the primary operating portion and the proximal end of the inserting portion. In the subsidiary operating portion, there are arranged a motor for rotating the ultrasonic vibrating element, a device for detecting the rotation of the motor, etc. Therefore, the forceps channel has to be provided in the subsidiary operating portion such that the channel does not interfere with various components. Thus, there is a problem that the forceps can not travel in the forceps channel so smoothly.

Further, the length of the forceps for endoscopes has a general standard. There is also a problem in that it is necessary to use the special long forceps having its length longer than the standard length.

In ultrasonic endoscopes, there has been suggested an apparatus having a balloon at the distal end of the inserting portion. In this apparatus, when diagnosis is conducted, a liquid is supplied into the balloon so that the ultrasonic wave is effectively propagated therethrough.

U.S. Pat. No. 4,433,692 and German Patent Laid-open Publication No. 3716963 disclose ultrasonic diagnostic apparatuses in which the ultrasonic vibrating element is provided at the distal end of the inserting portion and the head of the inserting portion is covered with a balloon. When diagnosis is conducted, the balloon is filled with an ultrasonic wave propagating liquid medium so that the outer surface of the balloon is urged against the inner wall of the cavity. Thus the ultrasonic wave is not so attenuated when it propagates in the medium so that the ultrasonic diagnosis can be carried out effectively. In order to operate the apparatus effectively, the ultrasonic propagating liquid medium has to be supplied to and exhausted from the balloon smoothly. In the ultrasonic diagnostic apparatus, it is also required to provide a suction device for sucking and removing obstacles existing in the cavity through a suction channel connected to the device. Therefore, in the ultrasonic diagnostic apparatus, there is a necessity to provide two suction means one of which is for sucking the liquid in the balloon and the other of which is for sucking the obstacles in the cavity. In Japanese Patent Laid-open Publication Kokai Sho No. 58-65,129, these two suction devices are integrated to one device, so that the operating efficiency is increased.

Heretofore, the ultrasonic endoscope in which the suction channel for sucking obstacles in the cavity is commonly used as the forceps channel is desired and practiced. In such endoscope, the forceps are inserted through the suction channel to effect the endoscopic treatment, for example biopsy for the tissues of the cavity.

However, at the distal end of the inserting portion of the conventional ultrasonic diagnostic apparatus having the balloon, if the suction channel is commonly used with the forceps channel, there would be problems as follows. That is to say, in case the liquid in the balloon is exhausted and the obstacles in the cavity are sucked by only one suction device, since the switching device of said suction device is located closer to the inserting portion than the position of the forceps opening, the forceps have to travel through the switching device to the distal end of the inserting portion. Thus, the forceps are sometimes obstructed from being inserted in the channel smoothly. In accordance with the position of the switching device, the forceps could not be inserted. Also, there is another problem in that when the forceps is inserted in the channel, the liquid in the balloon cannot be sucked therefrom.

SUMMARY OF THE INVENTION

The present invention has for its primary object to provide an endoscope apparatus having a forceps channel through which forceps having a standard length can be inserted smoothly.

The second object of the present invention is to provide an endoscope apparatus in which forceps can be smoothly inserted into the inserting portion irrespective of the state of the suction switching device and furthermore even when the forceps is inserted in the channel the liquid in the balloon can be exhausted to the outside of the apparatus.

The endoscope apparatus according to the invention comprises:
  an inserting portion insertable in a cavity under inspection and having distal and proximal ends;
  a forceps channel formed within the inserting portion to extend from said distal end to said proximal end;
  a subsidiary operating portion having one end connected to said proximal end of the inserting portion and the other end; and
  a primary operating portion having one end connected to the other end of said subsidiary operating portion: wherein said forceps channel is further extended to the subsidiary operating portion, and a proximal end opening of the forceps channel is arranged in the subsidiary operating portion at a more distal side than a junction portion between the primary operating portion and the subsidiary operating portion.

In a preferred embodiment of the apparatus according to the invention, an ultrasonic vibrating element is rotatably arranged at the distal end of the inserting portion, a shaft, one end of which is connected to said ultrasonic vibrating element, is extended through the inserting portion, a motor, to which the other end of the shaft is connected, for rotating said shaft and said ultrasonic vibrating element is arranged in the subsidiary operating portion, a balloon is provided at the distal end portion of the inserting portion, a liquid supply tube and a liquid drain tube, each having one end connected to the balloon, are extended through the inserting portion, the other end of the liquid supply tube is connectable to an ultrasonic propagating liquid medium supplying device and the other end of the liquid drain tube is connectable to a suction device so that the ultrasonic propagating liquid medium is supplied into and exhausted from the balloon via these tubes, a three-way valve is arranged between said liquid drain tube and the suction device, the forceps channel is arranged to be connectable to the suction device via the three-way valve, and thus obstacles in the cavity can be exhausted by means of the forceps channel.

BRIEF DESCRIPTION OF THE DRAWINGS

FIGS. 1-4 show one embodiment of the endoscope apparatus according to the present invention, and FIG. 1A is a schematic view illustrating a whole construction of the apparatus, FIGS. 1B and 1C are cross sectional views cut along B—B line and C—C line in FIG. 1A, respectively, FIG. 2 is a schematic view for explaining a driving means for driving an ultrasonic vibrating element, FIG. 3 is a schematic view showing the state that a top of the forceps is projected from an opening formed at the hard distal portion of the inserting portion, and FIG. 4 is a perspective view illustrating an overall construction of an observing system for observing ultrasonic and optical images of the cavity;

FIG. 6 is a schematic view showing a construction of still another embodiment of the apparatus according to the present invention;

FIG. 7 is a cross sectional view representing the primary portion of a fluid system of the embodiment shown in FIG. 6; and FIG. 8 is a cross sectional view illustrating the structure of the distal portion of the inserting portion of the modified embodiment of the apparatus shown in FIG. 6.

DETAILED DESCRIPTION OF THE PREFERRED EMBODIMENT

Figure 4:
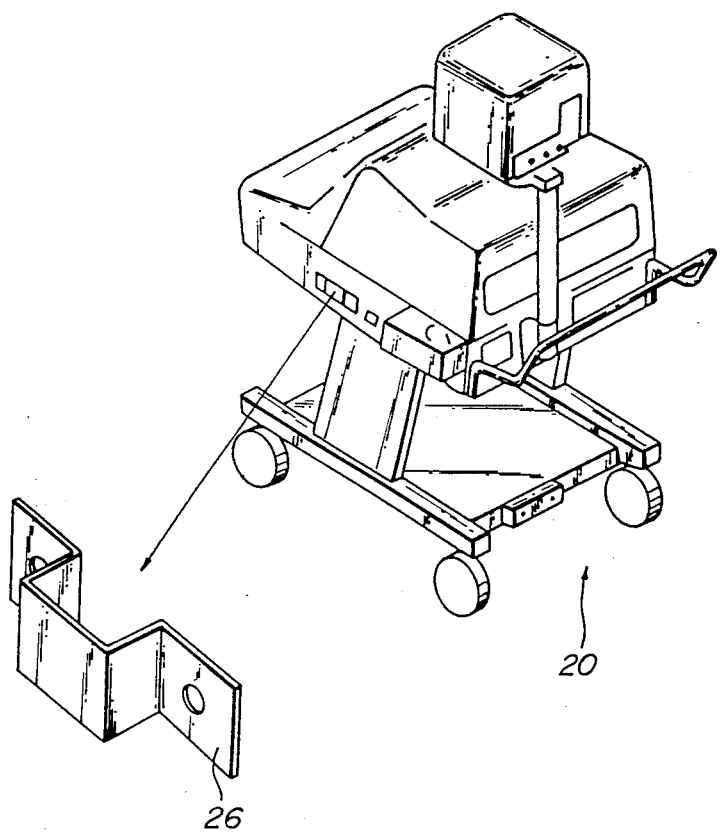

FIGS. 1-4 show a first embodiment of the ultrasonic endoscope apparatus according to the present invention. FIG. 1A is a schematic view showing a whole construction of the apparatus. In this figure, the numerical number 1 denotes a primary operating portion, 2 a flexible inserting portion, 3 a subsidiary operating portion, and 4 a junction portion for connecting said primary and subsidiary operating portions to each other. The inserting portion 2 is operated by the primary operating portion 1. The inserting portion 2 comprises a flexible tube portion 5, a bending portion 6 and a top hard portion 7 in the order from the proximal end thereof. The bending portion 6 is operated to be bent by operating a handle 8 provided on the primary operating portion 1. The inserting portion 2 has an ultrasonic vibrating element provided at the distal end thereof, and the element is rotated by means of the subsidiary operating portion 3 to effect the mechanical scan. In the subsidiary operating portion 3, a motor 10 is provided, and the driving power generated by the motor 10 is transmitted to an output shaft 11 via a decelerating device consisting of a pair of pulleys and a belt as shown in FIG. 2. Reference number 12 represents a rotation detecting device for detecting the rotation of the output shaft 11. The subsidiary operating portion 3 includes a pair of casings 9a and 9b. In the inserting portion 2, a flexible shaft 13 is extended to the ultrasonic vibrating element 14, and the output shaft 11 and the ultrasonic vibrating element 14 are connected to each other by the flexible shaft 13. As illustrated in FIG. 1C, an opening 15a of a tube 15 constituting a forceps channel is formed at a slant upper portion of the subsidiary operating portion 3, so that the forceps can be inserted in the forceps channel without being bent sharply. The forceps channel is extended to the top hard portion 7, and the top end portion 28 of the forceps is projected from an exit 16 formed in the side wall of the hard top portion 7, as shown in FIG. 3. When the forceps is inserted in the forceps channel, the top end portion 28 is abutted to a wall 17 and then is deflected to the outside of the top hard portion 7. Also, an injection channel for introducing the degassed water into the cavity is extended through the inserting portion 2 from a degassed water injection opening 27 formed at a lower portion of the subsidiary operating portion 3 to the top hard portion 7. Further, the forceps tube 15 is connectable to a suction device via a tube 30 and a valve 29.

A flexible universal tube 18 incorporating various kinds of members such as an air supply tube, a water supply tube, a suction tube and a light guide fiber bundle therein and a flexible cable tube 19 incorporating a signal cable connected to the ultrasonic vibrating element therein are connected to the primary operating portion 1. Said flexible universal tube 18 is connectable to a light source device (not shown) via a connector 18, and said flexible cable 19 is connectable to an ultrasonic observing device 20 shown in FIG. 4 via a connector 19a, respectively. As seen from FIGS. 1A and 1B, on the way of said cable tube 19, an intermediate box 23 is provided. In this box 23, there is provided a circuit substrate 22 including electric circuits for controlling the motor 10 provided in the subsidiary operating portion 3 and transmitting and receiving the ultrasonic pulse of the ultrasonic vibrating element. The intermediate box 23 comprises a couple of covers 24a and 24b, and on the outside wall of the cover 24a, a hook 25 is provided so as to hang the box 23 on the outside wall of the ultrasonic observing device 20 by coupling the hook 25 with a hook receiver 26, illustrated in FIG. 4.

Since a apparatus has the construction as described above, the forceps can be inserted smoothly into the inserting portion 2 from the opening 15a formed in the subsidiary operating portion 3, and the top end of the forceps is projected from the opening 16 formed in the top hard portion 7 of the inserting portion 2, so that living tissues in the cavity can be collected easily. In this case, since the top end of the forceps is first abutted on the wall 17 and thereafter is projected into the inside of cavity, the operator can obtain a clicking feeling and thus the operator can know instantly when the top end is projected into the inside of the cavity. In this manner, the operator can recognize the condition of the forceps, and the operation with the aid of the forceps is easier and more accurate. As described above, since it is possible to insert the forceps in the inserting portion from the subsidiary operating portion 3, the conventional problem wherein the forceps has to take a long sharply circuitous route when it travels through the subsidiary operating portion via the connecting portion 4, can be solved. And thus, the forceps can be smoothly and easily inserted into and pulled out of the forceps channel. In the conventional apparatus, the forceps is required to have a long length, because the forceps has to pass through the subsidiary portion 3. In contrast thereto, in the apparatus according to the present invention, it is possible to insert the forceps from the opening formed in the subsidiary portion 3, so that existing forceps having an ordinary length can be used, and it is not necessary to prepare the special forceps having a length longer than the standard length.

When diagnosis is being effected with the aid of ultrasonic waves, degassed water is supplied via a degassed water supply opening 27 by using a syringe, etc., connected thereto. In this case, since the degassed water supply opening 27 is formed in the lower portion of the subsidiary portion 3 and the casings 9a and 9b are coupled with each other tightly, if the degassed water is leaked from the syringe, etc., the leaked water might not be introduced into the subsidiary portion 3.

Furthermore, when the ultrasonic wave operating mechanism is to be adjusted or repaired, the adjusting or repairing can be conducted under the condition that the cover 24b is taken off and the intermediate box 23 is hung on the ultrasonic observing device by means of the hook 25 and the hook receiver 26. Therefore, the adjusting or repairing can be carried out more speedily and easily.

Moreover, after observing the ultrasonic image, if the valve 29 provided in the subsidiary operating portion 3 is switched to connect the suction device to the forceps channel, the degassed water could be exhausted from the cavity by using the forceps channel 15 as the suction channel. In this case, in order to prevent the air from being sucked through the forceps opening 15a, the opening has to be closed with a rubber plug.

Figure 5:
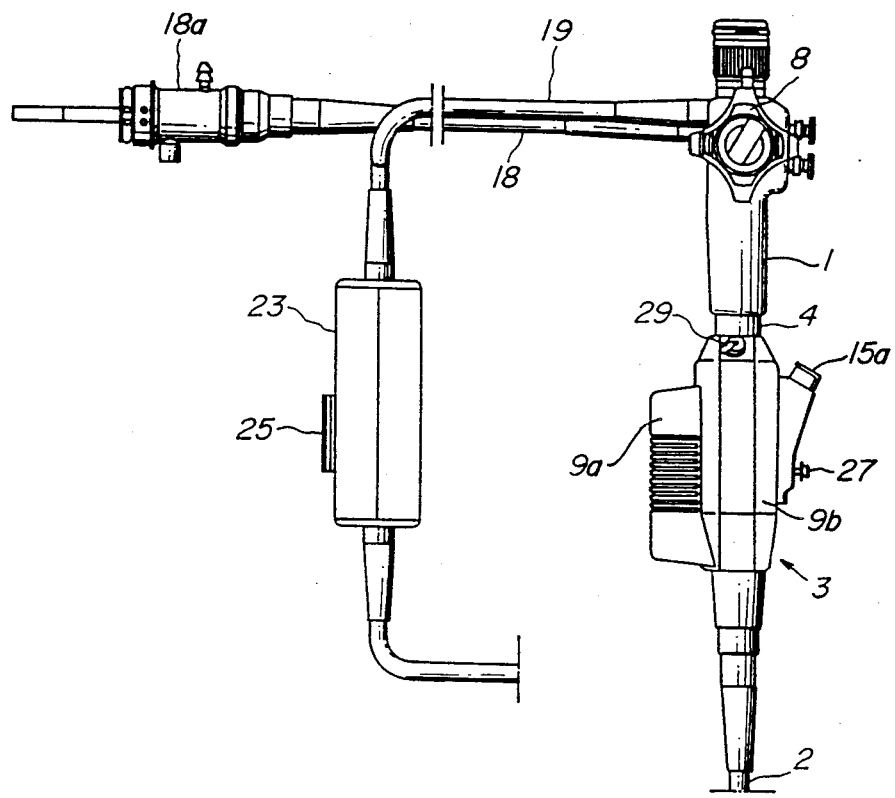
FIG. 5 is a schematic view depicting a construction of another embodiment of the apparatus according to the invention.

FIG. 5 is a schematic view illustrating the second embodiment of the apparatus according to the present invention. In this embodiment, the forceps opening 15a is formed in the casing 9b at the position opposite to the casing 9a in the subsidiary operating portion 3. In this apparatus, it is also possible to insert the forceps into the forceps channel from the upper side of the subsidiary operating portion. Of course, the same effect as the first embodiment can be obtained by this embodiment.

FIG. 6 is a schematic view representing the overall structure of the third embodiment of the apparatus according to the present invention. In FIG. 6, portions similar to those of the previous embodiments are denoted by the same reference numbers used in the previous embodiments, and the explanation thereof is omitted. In this embodiment, a balloon 31 made of resilient expandable material such as rubber is provided at the top hard portion 7 of the inserting portion 2 so as to surround the ultrasonic head.

FIG. 7 is a cross sectional view showing the principal part of the apparatus of this embodiment. A liquid supply channel 32 and a liquid drain channel 33 are respectively formed in the top hard portion 7 and openings 32a and 33a thereof are formed on the circumferential wall of the top hard portion. The liquid is supplied into and exhausted from the balloon 31 provided outside the top hard portion through the channels 32 and 33. The opening 34a of the forceps channel 34 is formed in the side wall of the top hard portion 7. A liquid supply tube 35 is connected to the liquid supply channel 32, a liquid drain tube 36 is connected to the liquid drain channel 33, and a forceps tube 15 is connected to the forceps channel 34, and these tubes 32, 33 and 34 are extended through the inserting portion 2. The forceps tube 15 is extended up to the forceps opening 15a and further connected to a three-way valve 37 via a tube 30 as shown in FIG. 7. In this embodiment, the three-way valve 37 is further connected to the liquid drain tube 36. The liquid supply tube 35 is connectable to the degassed water injection opening 27, which is provided in the subsidiary operating portion 3. The balloon 31, provided at the top hard portion 7 of the inserting portion 2, is made of resilient material, for example, rubber. The balloon has a cylindrical shape and has ring portions 31a and 31b which are resiliently clamped into slits formed on the circumferential wall surface of the top hard portion 7 in a liquid tight manner. And thus, it is possible to exchange the balloon easily.

The change-way valve 37 has three ports coupled with the tubes 30, 36 and 38, so that the tube 30 and liquid drain tube 36 are selectively connected to the suction tube 38, which is connectable to the suction device by rotating the lever 37 of valve by 90°.

In the structure of the third embodiment as described above, in case the obstacles in cavity are to be sucked out, the lever of the three-way valve 37 is rotated into the position shown in FIG. 7 to connect the forceps channel 34 to the suction device via the forceps tube 15 and the tube 30. After supplying the ultrasonic propagating medium liquid to the balloon 31 via the degassed water injecting opening 27 and the liquid supply tube 35 and observing the cavity, the three-way valve 37 is changed to connect the liquid drain tube 36 to the suction device via the suction tube 38, and then the degassed water is exhausted from the balloon. Further, when the forceps is used, the forceps is inserted into the forceps channel 15 via the forceps opening 15a, and the top portion of the forceps is projected into the cavity from the opening 34a formed in the top hard portion 7. In this case, since the lever 37a of the three-way valve 37 is not at the position shown in FIG. 7, the forceps can be inserted into the inserting portion even at the same time that the liquid is exhausted from the balloon 31 via the tube 36.

FIG. 8 is a schematic view illustrating the fourth embodiment of the apparatus according to the present invention. In this figure, the same reference numbers are used to denote the portions corresponding to those of the third embodiment shown in FIG. 7. In the present embodiment, instead of a mechanical scan, use is made of an electronic scan, so that the ultrasonic vibrating device 41 comprises an array of ultrasonic vibrating elements. A signal cable 42 is connected to the back side of the ultrasonic vibrating device 41 and is extended through the inserting portion 2. And the opening 34a of the forceps channel 34 is formed at the distal end of the top hard portion 7, and the balloon 31 is expanded only in the scanning direction. In such structure, the same effect as that of the third embodiment can be obtained.

The present invention is not limited to the above described embodiments and many alternations and modifications can be applied. For example, in the above embodiments the opening of the forceps channel is formed at the upper portion of the subsidiary operating portion which is close to the junction portion between the primary operating portion and the subsidiary operating portion, but it may be formed at the lower portion of the subsidiary operating portion closer to the junction portion between the subsidiary operating portion and the inserting portion. Also, in the subsidiary operating portion of the above embodiments, the driving device for rotating the ultrasonic vibrating element is provided, but other devices for carrying out various functions may be accommodated therein. Furthermore, while a cock-style valve is used for the valve mechanism, a piston may be used instead of the valve. In this case, it may be arranged that usually the suction channel is connectable to the suction device and the liquid drain channel is connected to the suction device by pushing the piston.

What is claimed is:

1. An endoscope apparatus for observing an inside of a cavity comprising:
    an inserting portion insertable in a cavity under inspection and having distal and proximal ends;
    an operating means having one end connected to said proximal end of said inserting portion;
    a forceps channel formed within the inserting portion to extend from said distal end to said proximal end and having a forceps opening formed in said operating means;
    a first conduit means arranged within said inserting portion;
    a suction source means for connection to one of said first conduit means and said forceps channel;
    a second conduit means provided in said operating means and having one end connected to said forceps channel at a point near said forceps opening and another end connected to said suction source means;
    a switching means arranged in said second conduit means for selectively alternately connecting one of said forceps channel and said first conduit means to said suction source means, regardless of whether a forceps is inserted into said forceps channel.

2. An apparatus according to claim 1, further comprising:
    an ultrasonic vibrating element arranged rotatably at the distal end of the inserting portion,
    a shaft having one end connected to the ultrasonic vibrating element and extending through the inserting portion, and
    a motor connected to the other end of said shaft and arranged in said operating means to rotate said shaft and said ultrasonic vibrating element connected thereto.

3. An apparatus according to claim 1 or 2, further comprising:
    a balloon arranged at the distal end of said inserting portion, a liquid supply tube and a liquid drain tube each having one end connected to the balloon, said second conduit means comprising said liquid drain tube, said liquid supply tube and said liquid drain tube extending through said inserting portion, said liquid supply tube having its other end connected to a liquid supply device for supplying ultrasonic transmitting medium liquid into the balloon and said liquid drain tube having its other end connected to said switching means to be connectable to said suction source to exhaust the ultrasonic transmitting medium liquid from the balloon.

4. An apparatus according to claim 3, wherein said switch means comprises a three-way valve.

5. An apparatus according to claim 4, wherein said three-way valve is arranged in the operating means.

6. An apparatus according to claim 1, wherein said inserting portion is arranged to be flexible, and an operating member is provided at said operating portion to bend the distal means of the inserting portion.

* * * * *